(12) United States Patent
Liversidge (10) Patent No.: US 7,815,610 B2
(45) Date of Patent: Oct. 19, 2010

(54) INJECTION APPARATUS

(75) Inventor: Barry Peter Liversidge, The Wick, Wick Road, Langham, Colchester, Essex (GB) CO4 5PE (73) Assignee: Barry Peter Liversidge, Colchester, Essex (GB)

( * ) Notice: Subject to any disclaimer, the term of this patent is extended or adjusted under 35 U.S.C. 154(b) by 0 days.

(21) Appl. No.: 11/675,743

(22) Filed: Feb. 16, 2007

(65) Prior Publication Data

US 2007/0156101 A1 Jul. 5, 2007

(51) Int. Cl.
  A61M 5/32 (2006.01)
  A61M 5/00 (2006.01)
  A61M 5/315 (2006.01)

(52) U.S. Cl. .................. 604/192; 604/218; 604/111

(58) Field of Classification Search ............ 604/111, 604/192, 197, 218, 198, 263, 46, 272; 220/296, 220/297, 300; 606/185; 206/365, 210, 305, 206/306, 338, 364
See application file for complete search history.

(56) References Cited

U.S. PATENT DOCUMENTS

| | | | | |
|---|---|---|---|---|
| 1,378,806 A | * | 5/1921 | Ausubel | 206/210 |
| 1,711,594 A | * | 5/1929 | Gillespie | 206/365 |
| 1,838,825 A | * | 12/1931 | Goldstein | 206/210 |
| 2,023,289 A | * | 12/1935 | Pringle | 206/229 |
| 2,400,722 A | * | 5/1946 | Swan | 206/210 |
| 3,008,570 A | * | 11/1961 | Roehr et al. | 206/229 |
| 3,244,272 A | * | 4/1966 | Beaman et al. | 206/0.82 |
| 3,272,322 A | * | 9/1966 | Ogle | 206/365 |
| 3,342,319 A | * | 9/1967 | Faulseit | 206/365 |
| 3,434,587 A | * | 3/1969 | Ciampa | 206/365 |
| 3,485,239 A | * | 12/1969 | Vanderbeck | 604/192 |
| 3,677,247 A | * | 7/1972 | Brown | 604/197 |
| 3,783,997 A | * | 1/1974 | Brown | 206/365 |
| 3,890,971 A | * | 6/1975 | Leeson et al. | 604/110 |
| 4,573,973 A | | 3/1986 | Mezi et al. | |
| 4,592,744 A | * | 6/1986 | Jagger et al. | 604/192 |
| 4,816,024 A | * | 3/1989 | Sitar et al. | 604/192 |
| 4,886,497 A | * | 12/1989 | Scholl, Jr. | 604/111 |
| 4,938,745 A | | 7/1990 | Sagstetter et al. | |
| 5,417,326 A | * | 5/1995 | Winer | 206/365 |

(Continued)

FOREIGN PATENT DOCUMENTS

WO 01/78806 10/2001

(Continued)

Primary Examiner—Kevin C Sirmons
Assistant Examiner—Michael J Anderson
(74) Attorney, Agent, or Firm—Andrus, Sceales, Starke & Sawall, LLP (57) ABSTRACT

Injection apparatus having a pre-filled syringe provided with a safety needle assembly, and a sleeve open at one end for containing the syringe with the safety needle assembly projecting from the open end of the sleeve. A cap is fitted to the open end and is configured to receive the projecting part of the safety needle assembly. A seal secures the cap to the sleeve. Following breaking of the seal, the syringe is removed from the sleeve and the cap is removed from the safety needle assembly so permitting the syringe to perform an injection. Thereafter, the syringe is reinserted into the sleeve with the safety needle assembly nearer the closed end of the sleeve, an internal rib in the sleeve co-operating with the safety needle assembly to retain that assembly in the sleeve.

16 Claims, 9 Drawing Sheets

U.S. PATENT DOCUMENTS

| | | | | |
|---|---|---|---|---|
| D364,501 S * | 11/1995 | Gough | ........................ | D3/203.8 |
| 5,611,429 A * | 3/1997 | Phillips | ........................ | 206/365 |
| 5,647,849 A * | 7/1997 | Kalin | ........................ | 640/111 |
| 5,665,071 A | 9/1997 | Wyrick et al. | | |
| 5,828,073 A * | 10/1998 | Zhu et al. | ........................ | 250/506.1 |
| 5,921,966 A * | 7/1999 | Bendek et al. | ........................ | 604/207 |
| 5,927,351 A * | 7/1999 | Zhu et al. | ........................ | 141/330 |
| 6,155,420 A * | 12/2000 | Phillips | ........................ | 206/364 |
| 6,159,184 A * | 12/2000 | Perez et al. | ........................ | 640/192 |
| 6,368,305 B1 * | 4/2002 | Dutton | ........................ | 604/192 |
| 6,379,330 B1 * | 4/2002 | Lund et al. | ........................ | 604/111 |
| 6,425,174 B1 * | 7/2002 | Reich | ........................ | 29/469 |
| 6,461,333 B1 * | 10/2002 | Frezza | ........................ | 604/192 |
| 6,576,918 B1 * | 6/2003 | Fu et al. | ........................ | 250/507.1 |
| 6,638,256 B2 * | 10/2003 | Jansen et al. | ........................ | 604/198 |
| 6,656,163 B1 * | 12/2003 | Marshall et al. | ........................ | 604/198 |
| D488,864 S * | 4/2004 | Fago et al. | ........................ | D24/121 |
| 6,722,499 B2 * | 4/2004 | Reich | ........................ | 206/365 |
| 6,726,649 B2 * | 4/2004 | Swenson et al. | ........................ | 604/46 |
| 6,929,126 B1 * | 8/2005 | Herbert | ........................ | 206/365 |
| 6,953,447 B2 * | 10/2005 | Aubert et al. | ........................ | 604/110 |
| 7,019,317 B1 * | 3/2006 | Martin et al. | ........................ | 250/506.1 |
| 7,040,856 B2 * | 5/2006 | Reich | ........................ | 414/810 |
| 7,086,133 B2 * | 8/2006 | Reich | ........................ | 29/426.3 |
| 7,268,359 B2 * | 9/2007 | Fu et al. | ........................ | 250/507.1 |
| 2003/0132128 A1 * | 7/2003 | Mazur | ........................ | 206/364 |
| 2004/0078005 A1 * | 4/2004 | Aubert et al. | ........................ | 604/198 |
| 2004/0167476 A1 * | 8/2004 | Westbye | ........................ | 604/192 |
| 2005/0148933 A1 * | 7/2005 | Raven et al. | ........................ | 604/111 |
| 2005/0165360 A1 * | 7/2005 | Stamp | ........................ | 604/187 |
| 2005/0165361 A1 * | 7/2005 | Marshall et al. | ........................ | 604/197 |
| 2005/0192534 A1 * | 9/2005 | Wolbring et al. | ........................ | 604/111 |
| 2005/0234424 A1 * | 10/2005 | Besing et al. | ........................ | 604/500 |
| 2005/0283116 A1 * | 12/2005 | Eakins et al. | ........................ | 604/111 |
| 2006/0282044 A1 * | 12/2006 | Mohammed | ........................ | 604/192 |
| 2007/0100290 A1 * | 5/2007 | Schiffmann et al. | ........................ | 604/198 |
| 2007/0129591 A1 * | 6/2007 | Yanke et al. | ........................ | 588/16 |
| 2008/0021413 A1 * | 1/2008 | Dos Santos et al. | ........................ | 604/218 |

FOREIGN PATENT DOCUMENTS

WO 04/000397 12/2003

* cited by examiner

INJECTION APPARATUS

This invention relates to injection apparatus and in particular to injection apparatus comprising a pre-filled injector together with a packaging sleeve therefor.

Medicaments in the form of a liquid may be administered to a human or animal body by means of an injector having a hollow needle, the injector including a source of the medicament. For example, the injector may be in the form of a small volume syringe holding the liquid medicament, the needle projecting from the forward end of the syringe and used to penetrate the body at the site at which the medicament is to be received.

There has been a trend towards self-administered drug delivery injector systems, for various reasons. Advances in drug technology have made possible the treatment of conditions which previously may not have been treatable, or only treatable with difficulty, leading to the need to deliver many drugs at frequent and regular intervals. Self administration has the advantage that a patient may perform the required injections wherever that patient happens to be, without the need to seek the services of a medically-qualified person. Also, self-injection reduces the work-load on the medical services.

It is an unfortunate fact that many people have an aversion to injections, and to needles in particular. In an attempt to alleviate this, there have been many developments in injector technology, such that a needle is obscured for at least part of an injection procedure, and in some cases for the whole of the procedure. In this way, a patient may not be able to see the needle and so find the procedure less distressing. Further, it becomes easier for a patient to undertake self-administration of drugs by injection, if the needle is obscured throughout the procedure.

An important part of an injection procedure is the safe disposal of the used injector and needle. In the case of self-administration, this becomes even more important, as non-qualified people could come into contact with the used equipment.

The present invention stems from research into ways in which an injection apparatus may be supplied to a patient ready to perform a self-administered injection, or to a person who will administer an injection to the patient, and then to dispose of the used apparatus, minimising the risk both to the patient and others from the used syringe and needle.

According to this invention, there is provided injection apparatus comprising:
an injector pre-filled with a medicament and including a cylindrical body provided with a safety needle assembly on its forward end and having a plunger projecting from its rearward end which plunger is provided with a piston for expelling medicament out of the safety needle assembly;
a sleeve open at one end and closed at the other end, the syringe initially being located in the sleeve with the plunger nearer the closed end of the sleeve and the safety needle assembly projecting from the open end of the sleeve;
a cap adapted to be fitted to the open end of the sleeve, the cap being configured to receive the safety needle assembly when fitted to the sleeve accommodating the syringe;
sealing means adapted to seal the cap to the sleeve; and
co-operable retaining means on the safety needle assembly and the inner surface of the sleeve nearer the closed end thereof;
the arrangement being such that following the breaking of the seal, the syringe may be removed from the sleeve and the cap from the safety needle assembly so permitting the syringe to be used to perform an injection, whereafter the syringe may be reinserted into the sleeve with the safety needle assembly nearer the closed end thereof, the co-operable retaining means then serving to retain the safety needle assembly in the sleeve.

With the injection apparatus of this invention, it becomes possible to provide a patient with a sterile injector assembly pre-filled with the required medicament and having a needle already fitted to the syringe so that the patient does not have to become involved with the fitting of a needle to a syringe. Then, following performance of the injection, the used syringe and needle may be disposed of in a safe manner, using the packaging in which the syringe and safety needle assembly were supplied, so minimising the risk of injury either to the patient or others.

The injector used in this invention may be an essentially conventional pre-filled syringe. Thus, the injector may have a cylindrical body typically of glass together with a plunger having a piston disposed within the cylindrical body whereby depression of the plunger expels medicament contained within the body. A needle may be pre-fitted to the forward end of the body during the manufacture of the syringe, before filling.

The safety needle assembly may take any known suitable form, and typically will have a sleeve which normally is in a projecting position where the sleeve surrounds and projects beyond the needle. The sleeve may be withdrawn from this projecting position so as to expose the needle and so permit the making of an injection. Then, following performance of the injection, the sleeve may move forward once more so as again to surround the needle, the sleeve then automatically locking-out so that it may not be withdrawn for a second time. Such safety needle assemblies are known in the art and will not be described in further detail here.

As an alternative to having the needle fitted to the forward end of the injector body during the manufacture thereof, the needle may be a part of the safety needle assembly, which assembly is fitted to the injector body following filling of the body with the medicament. Either way, the combination of the injector and the safety needle assembly is essentially the same and performs the same function.

The sleeve employed in this invention may be a simple tubular sleeve closed at one end and of a sufficient diameter to accommodate the injector body and the safety needle assembly fitted thereto. The length of the sleeve should be sufficient for the plunger to be accommodated in its initial projecting condition (i.e. before depression), but with at least a part if not all of the safety needle assembly projecting from the sleeve. Preferably, in order to give adequate location for the injector in the sleeve, a short portion of the safety needle assembly may be disposed within the sleeve, with the injection apparatus in its initial condition.

The cap must have a sufficient diameter to accommodate the safety needle assembly and also must be connectible to the open end of the sleeve. Thus, the cap may have a closed end and an open end, the open end being inter-engageable with the open end of the sleeve. For this purpose, the respective open ends may be provided with one of a simple plug-in connection, a screw-threaded connection, a bayonet connection and a snap-fitting connection.

The sealing means may perform three distinct functions. Firstly, the sealing means may serve to hold the cap to the sleeve or to prevent release of the cap from the sleeve, prior to use of the injection apparatus. Secondly, the sealing means may serve as a tamper-evident seal, such that it will be entirely obvious to an intending user if the cap has been removed from the sleeve, so giving access to the injector, prior to the intended first use of the injector. Thirdly, the sealing means may provide an essentially hermetic seal, in order to ensure the environment within the sleeve and cap remains sterile, until the injector is to be used.

The above functions may be fulfilled by means of a frangible or strippable seal wrapped wholly around and adhered to the junction between the sleeve and the cap. Such a seal advantageously is of a paper or plastics material and further carries relevant data such as the nature of the contained medicament and its volume, date of manufacture, and so on.

The co-operable retaining means provided between the safety needle assembly and the sleeve conveniently is defined by the provision of an interference fit between the outer surface of the safety needle assembly and the inner surface of the sleeve, in the region of the closed end thereof. Thus, by having the bore of the sleeve tapering slightly towards the closed end thereof, it becomes possible easily to insert the safety needle assembly into the open end of the sleeve, increasing pressure being required to drive the safety needle assembly towards the closed end of the sleeve. When fully there, it will be significantly difficult to remove the injector assembly from the sleeve since access can be gained solely to the plunger head, which in any event should be located within the sleeve. If an attempt is made to remove the injector from the sleeve by pulling on the plunger, all that is likely to happen is that the plunger will come out of the injector body, so still leaving that body and the used safety needle assembly within the sleeve.

As an alternative to having an interference fit between the safety needle assembly and the bore of the sleeve, a more positive inter-engagement between the safety needle assembly and the sleeve may be provided. For example, an annular rib may be formed internally within the sleeve, at such a location that the safety needle assembly may pass over that rib and a shoulder of that assembly then locates behind the rib so as thereafter to resist withdrawal of the assembly from the sleeve. The shoulder may be formed by a rear end plane of the safety needle assembly or by a groove formed therearound, within which the rib may locate. In another possibility, the safety needle assembly may have a barb-like formation on the outer surface thereof which formation is inter-engageable with a corresponding formation on the inner surface of the sleeve, in the region of the closed end thereof.

By way of example only, one specific embodiment of injection apparatus of this invention will now be described in detail, reference being made to the accompanying drawings in which.

Figure 1:
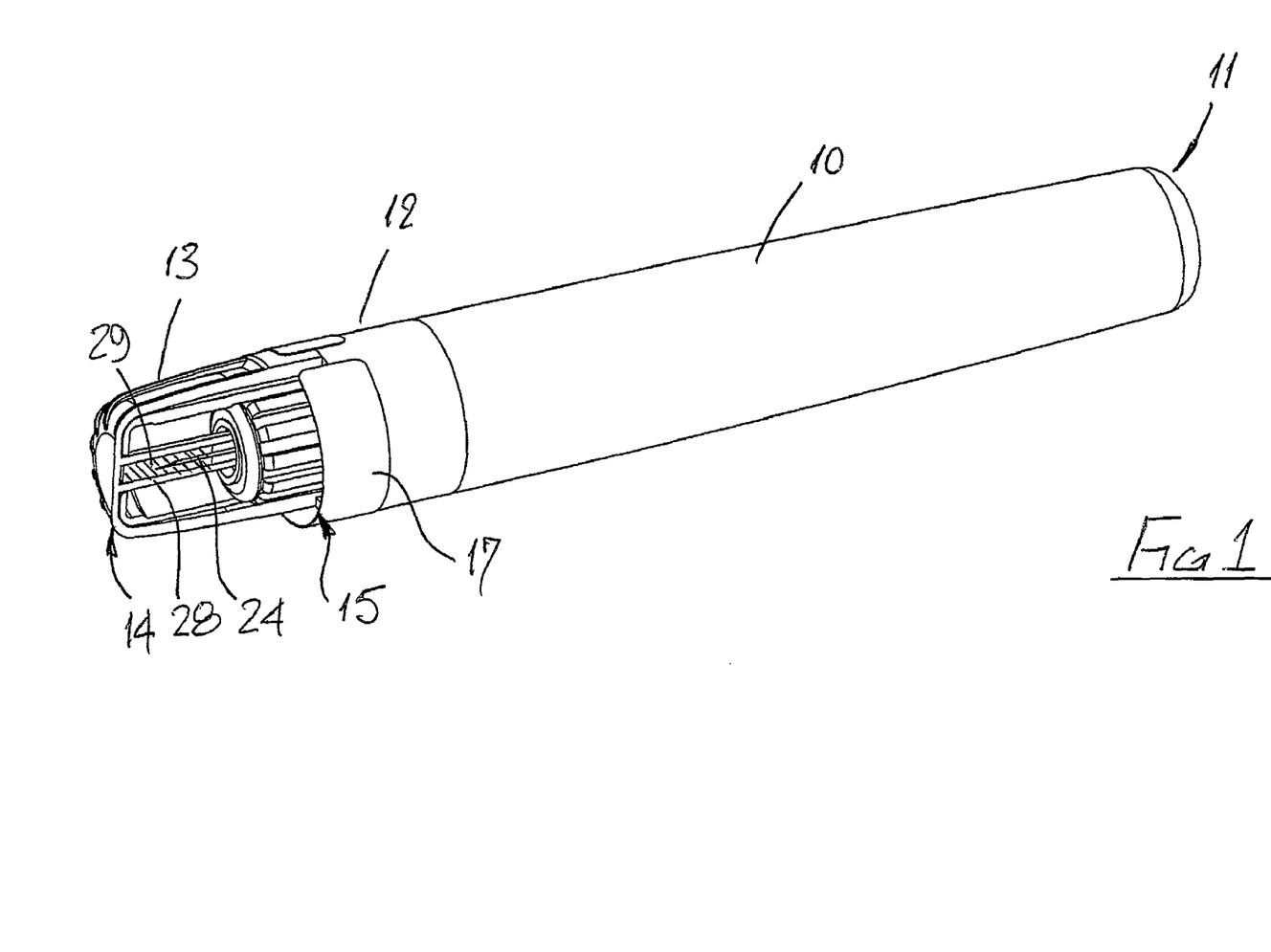
FIG. 1 is an isometric view of the apparatus in its initial condition but with the cap partly cut away to show certain internal details.

FIG. 1 shows the initial assembly of the embodiment of injection apparatus of this invention, partly in section. This assembly comprises a tubular sleeve 10 having a closed end 11 and an open end 12. A cap 13 is fitted to the open end, that cap also having a closed end 14 and an open end 15. At the open end of the cap, there is a projecting rim 16 of a reduced diameter, for accommodation within the open end 12 of the tubular sleeve 10. Though not shown, the rim 16 may be provided with an external screw-thread, engageable with an internal screw-thread formed within the open end of the sleeve. An adhesive plastic seal 17 extends around and bridges the junction between the sleeve 10 and the cap 13. That presence of that seal thus indicates that the cap has not previously been removed from the sleeve and further serves to provide a hermetic seal to ensure the content of the sleeve remains in a sterile condition.

Figure 2:
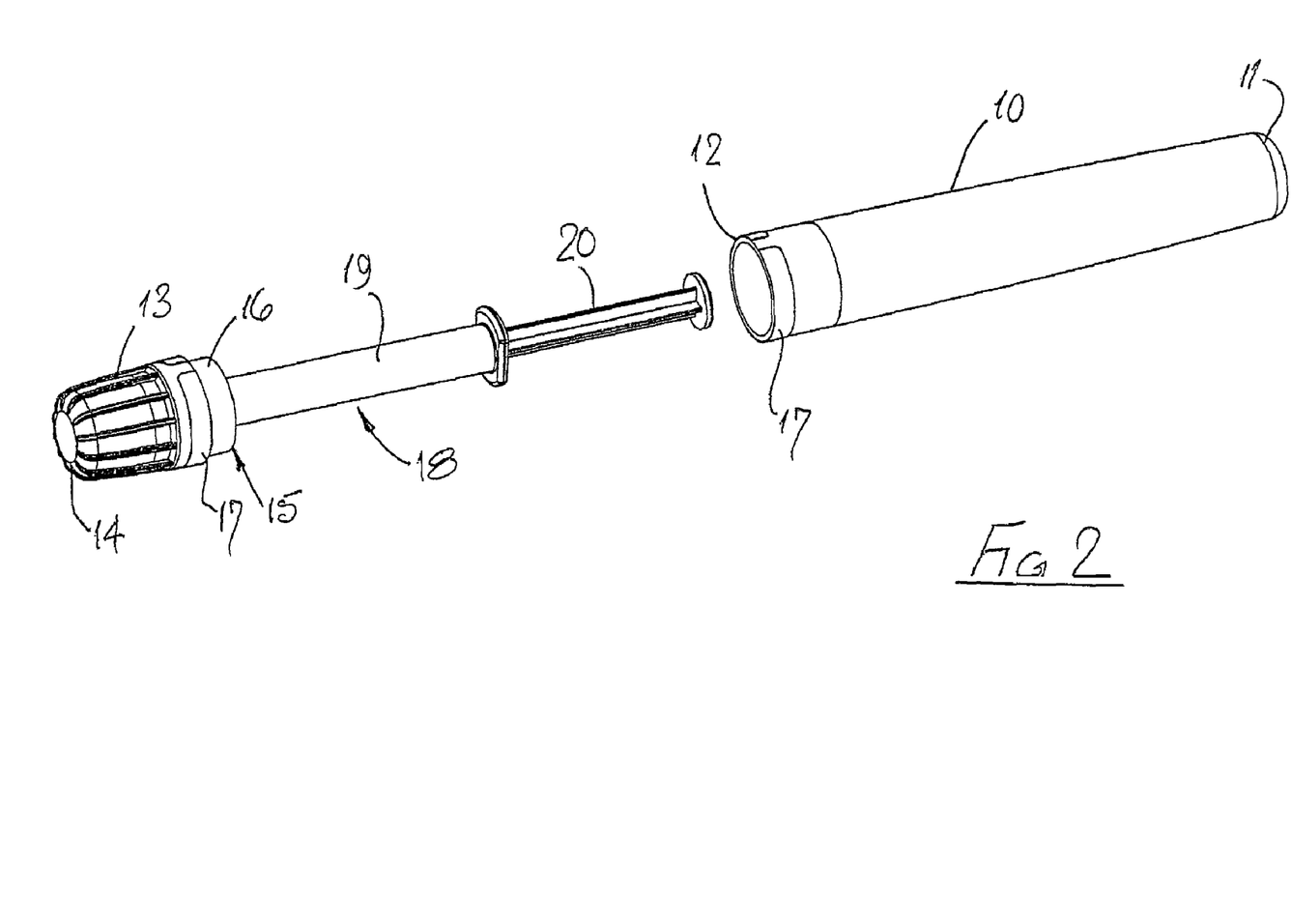
FIG. 2 shows the apparatus of FIG. 1, but with the injector and cap removed from the sleeve.

In order to open the package defined by the sleeve 10 and cap 13, the seal is either removed or otherwise broken, so then permitting the cap 13 to be moved away from the sleeve 10, the cap taking with it an injector 18 the bulk of which was previously accommodated within the sleeve 10 (FIG. 2). The injector comprises a tubular body 19 containing a medicament to be injected, a plunger 20 extending away from the rearward end of the body and having a piston provided within the body so that depression of the plunger will expel contained medicament out of the forward end of the body.

Figure 3:
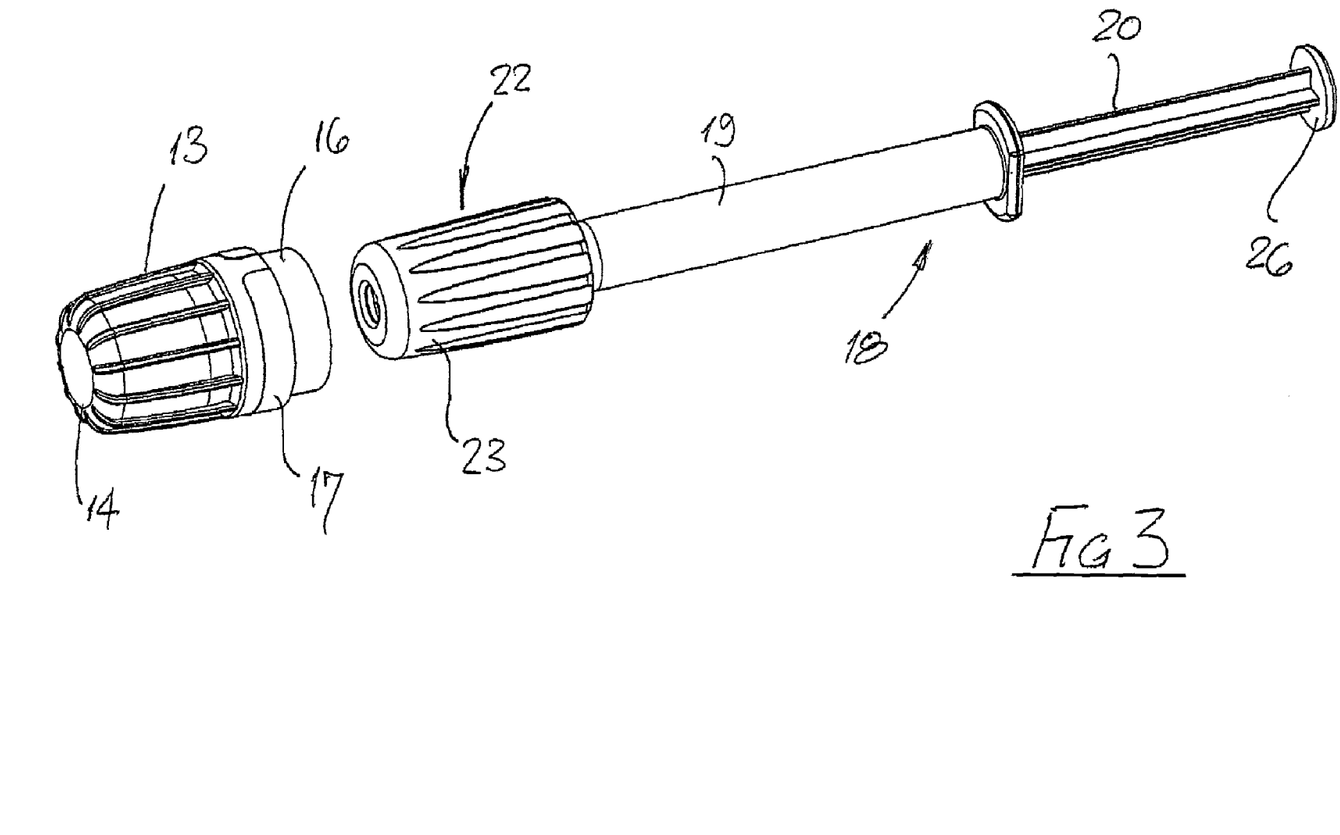
FIG. 3 shows the injector with the cap removed therefrom.
Figure 4:
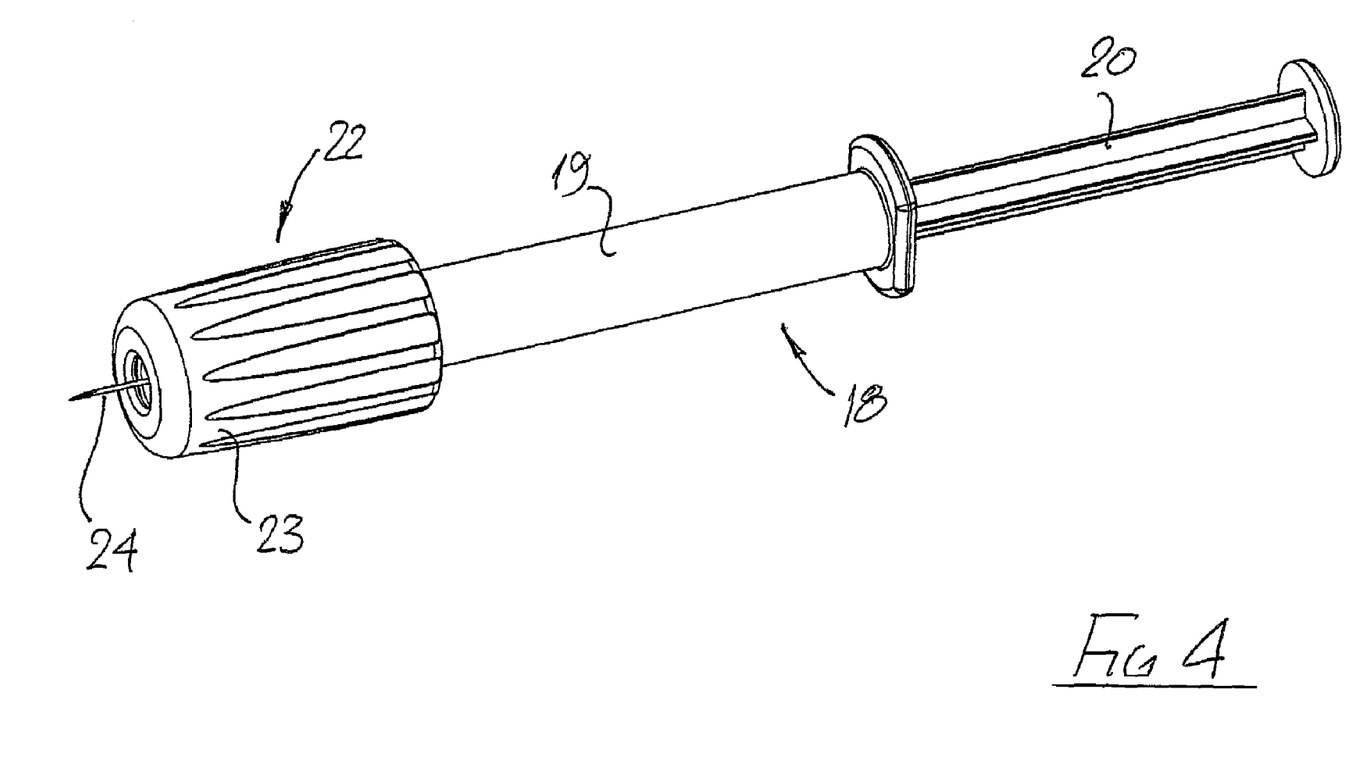
FIGS. 4, 5 and 6 show successive stages in the administering of an injection with the injector.
Figure 5:
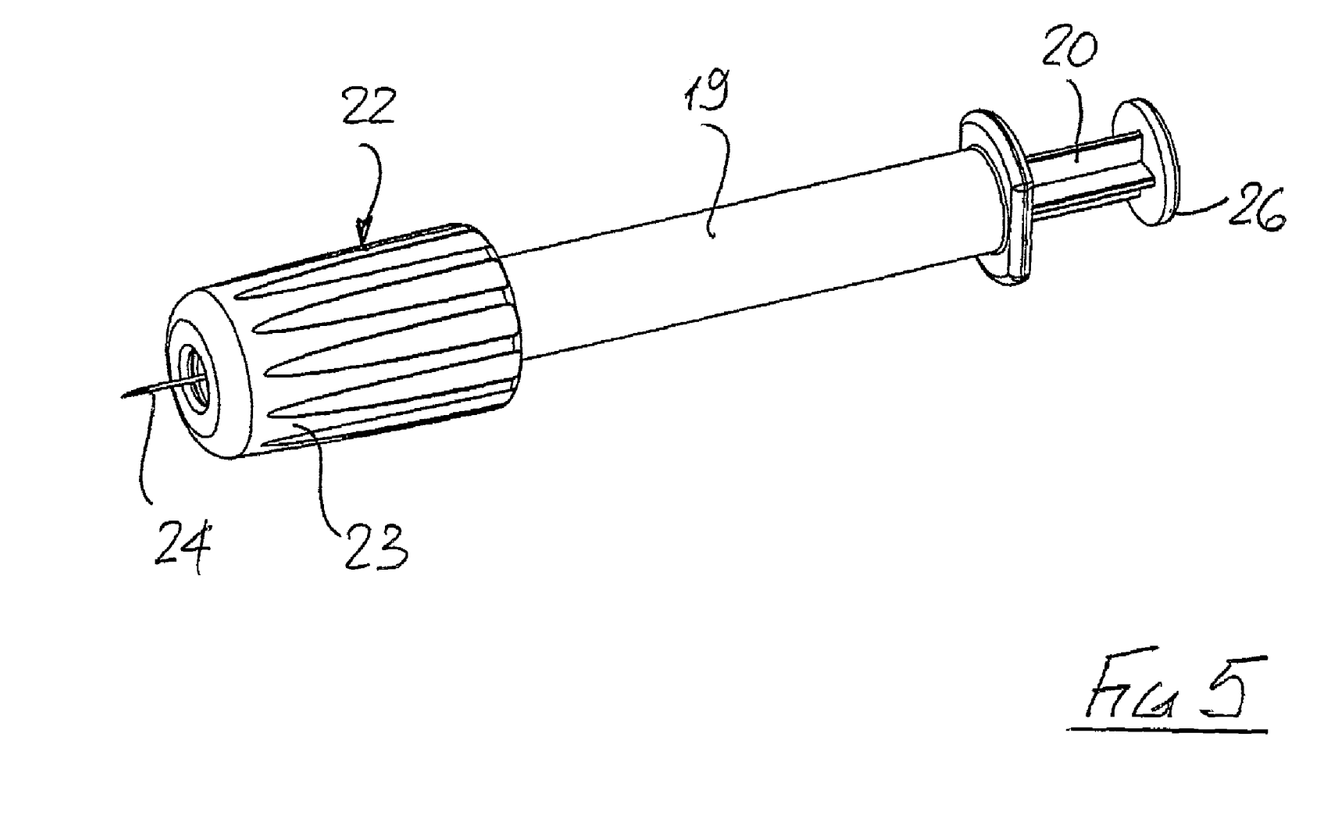
Figure 6:
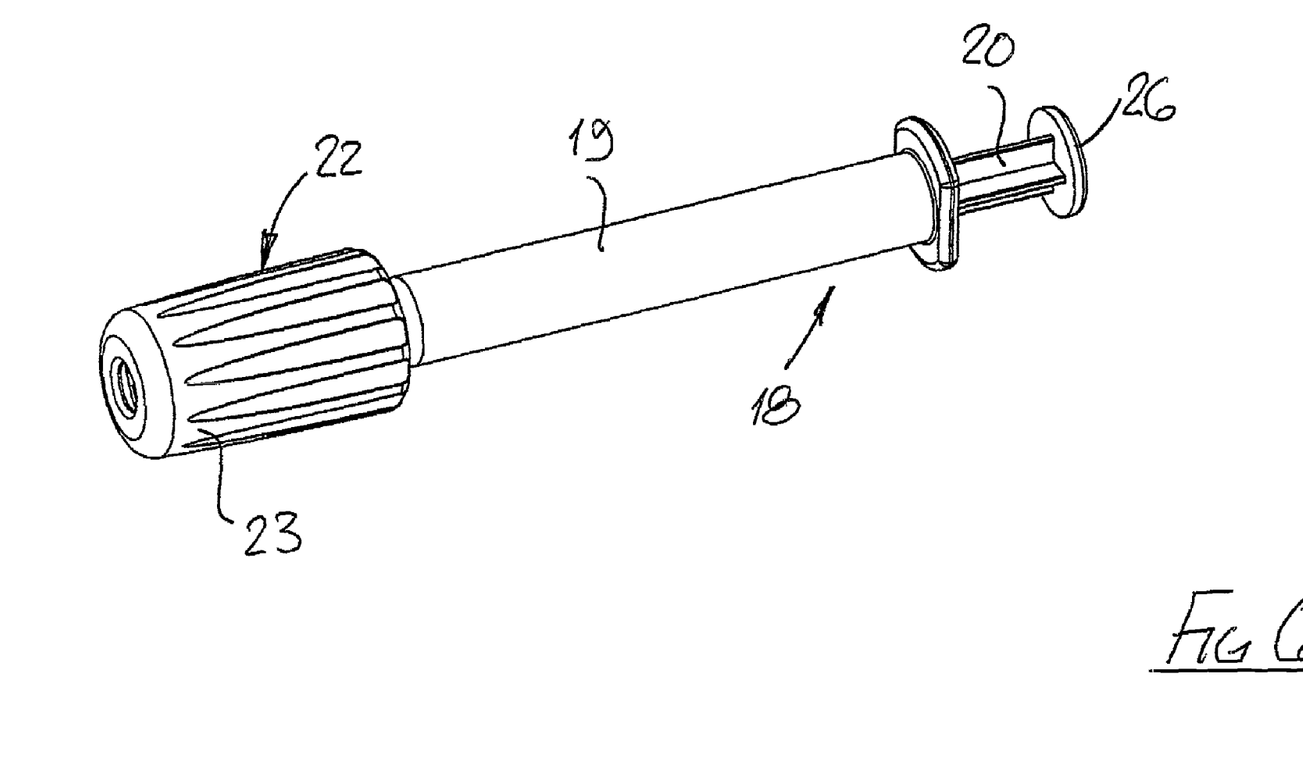

The cap 13 is then removed from the forward end of the injector (FIG. 3), so exposing a safety needle assembly 22. Such an assembly may take any known form and typically has a tubular guard 23 which projects forwardly from the injector body, so as to protect a needle 24 contained therewithin. The sleeve may move rearwardly from this initial position of FIG. 3, as shown in FIG. 4, so as to expose the needle and thus permit the performance of an injection, by depressing the plunger 20 into the injector body 19 (FIG. 6). On completion of the injection and removal of the syringe from the injection site, the tubular guard 23 may move forwardly once more (FIG. 6) so as once more to surround and protect a needle contained therewithin, the guard 23 then locking out so as to be prevented from moving rearwardly for a second time.

Figure 7:
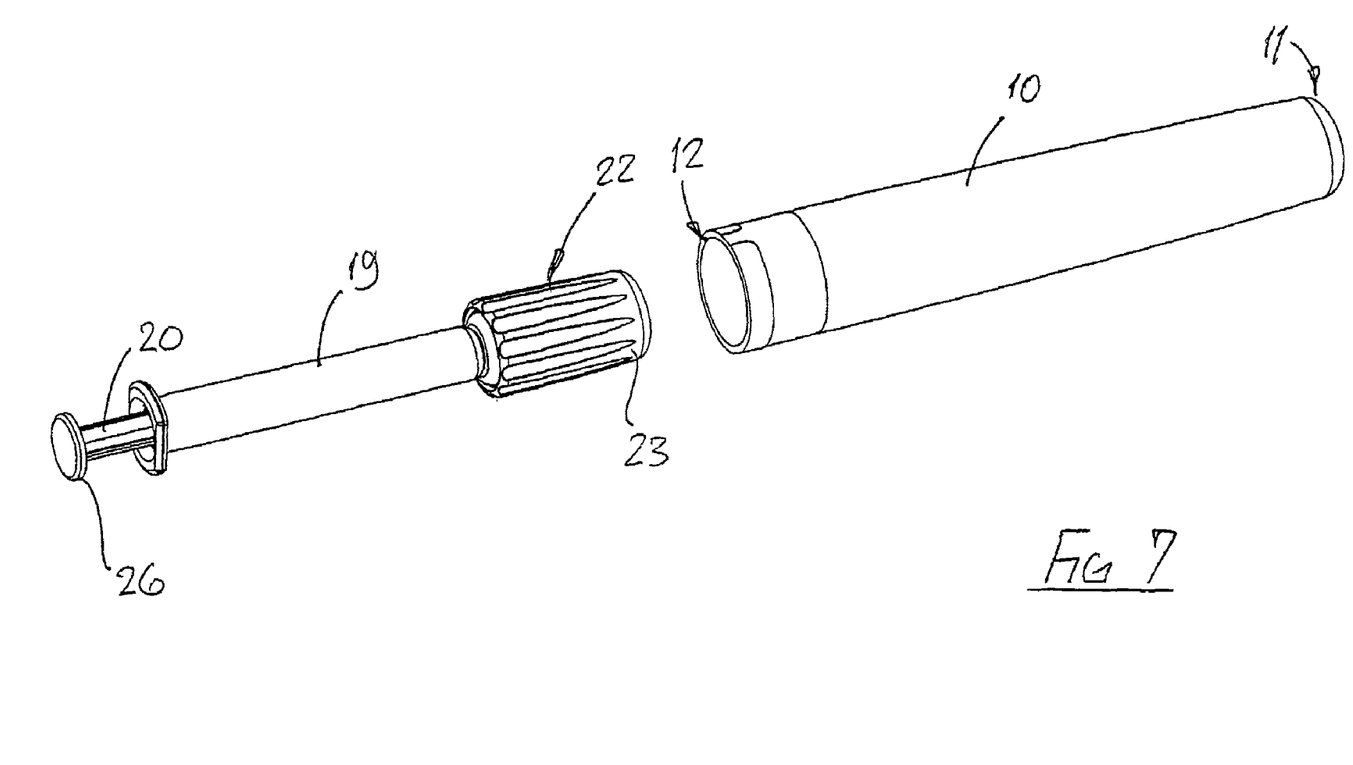
FIG. 7 shows the used injector being re-inserted into the sleeve, with the safety needle assembly leading.
Figure 8:
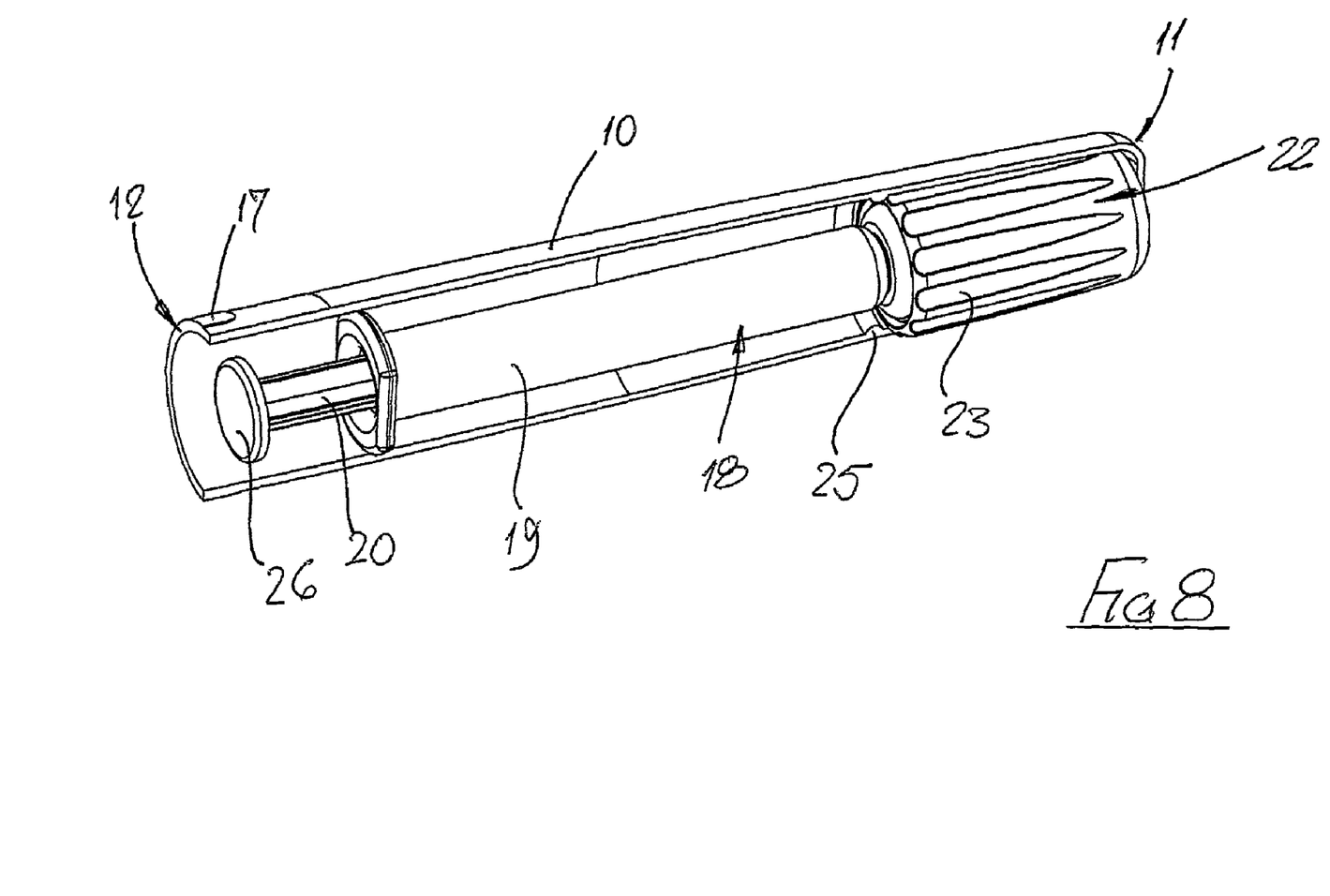
FIG. 8 is a part-sectional view, showing the used injector fully accommodated within the sleeve.

The injector assembly is then offered to the sleeve 10 but with the safety needle assembly 22 leading, so as to enter the open end 12 of the sleeve (FIG. 7). The injector is pushed fully into that sleeve (FIG. 8), the safety needle assembly 22 riding over an annular rib, shoulder or similar abutment 25 provided within the sleeve at a distance from the closed end thereof slightly greater than the length of the safety needle assembly. Thus, when pushed fully into the sleeve, the safety needle assembly will be disposed wholly beyond the rib 25 which should be profiled to trap the safety needle assembly within the sleeve. As shown in FIG. 8, when in this condition, the entire injector assembly is disposed within the sleeve. Any attempt to remove the assembly for example by pulling on the head 26 of the plunger (being the most accessible component) will simply pull the plunger out of the syringe body 19.

Figure 9:
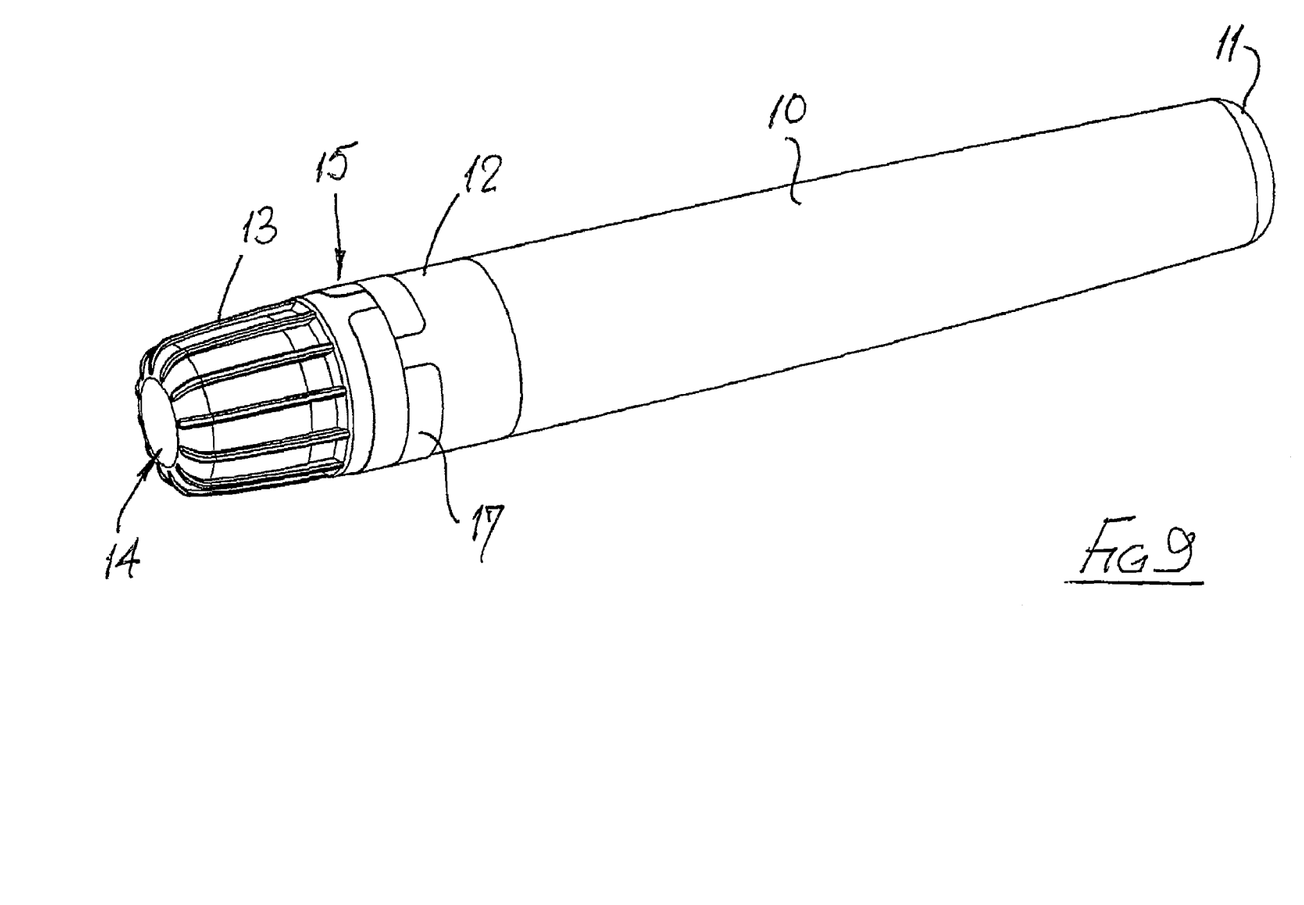
FIG. 9 shows the cap re-fitted to the sleeve such that the entire assembly is now ready for disposal.

Finally, the cap 13 may be re-fitted to the sleeve as shown in FIG. 9 so making a compact package wholly containing the used injector, ready for disposal. In this connection, the assembly as shown in FIG. 9 essentially corresponds to the initial condition as shown in FIG. 1, except that the seal 17 has been broken, in FIG. 9.

Referring once more to FIG. 1, it can be seen that a tube 28 projects internally from the closed end 14 of the cap 13 and accommodates the needle 24, until the cap is removed from the safety needle assembly. That tube 28 may also serve to maintain the safety needle assembly in an initial condition and to prevent the assembly locking out for example during transit, which otherwise might render the injector unusable. The tube 28 contains a plug 29 of soft pliable material such as of silicone rubber, to effect a seal to the needle, thereby to prevent medicament leaking out of the needle and also to prevent the medicament being contaminated by the ingress of foreign matter through the needle.

The invention claimed is:

1. Injection apparatus comprising:
   (a) an injector assembly comprising:
      an injector pre-filled with a medicament and including a cylindrical body, a safety needle assembly provided on the forward end of the cylindrical body, and a plunger projecting from the rearward end of the cylindrical body, a piston being provided on the plunger for expelling medicament out of the safety needle assembly; and
   (b) packaging for said injector assembly comprising:
      a sleeve open at one end and closed at the other end, said sleeve removably receiving said injector therein, said injector initially being located in the sleeve with the plunger nearer the closed end of the sleeve and the safety needle assembly projecting from the open end of the sleeve, said sleeve surrounding and enclosing at least the cylindrical body and plunger of said injector;
      a cap adapted to be fitted to the open end of the sleeve, the cap being configured to receive the safety needle assembly when said cap is fitted to the sleeve accommodating the injector;
      seal means for sealing the cap to the sleeve; and
      co-operable retention means for acting between the safety needle assembly and the inner surface of the sleeve nearer the closed end thereof to retain the safety needle assembly in the sleeve at the closed end thereof;
      the arrangement being such that following the breaking of the seal, the injector is removable from the sleeve and the cap is removable from the safety needle assembly so permitting the injector assembly to be used to perform an injection, whereafter the injector is reinsertable into the sleeve with the safety needle assembly nearer the closed end thereof, the co-operable retention means then serving to retain the safety needle assembly in the sleeve.

2. Injection apparatus as claimed in claim 1, wherein the co-operable retention means is defined by an interference fit between the outer surface of the safety needle assembly and the inner surface of the sleeve, adjacent the closed end thereof.

3. Injection apparatus as claimed in claim 1, wherein the co-operable retention means is defined by a rib formed internally within the sleeve part-way along the length thereof and over which the safety needle assembly is drivable so as to be positioned between the closed end of the sleeve and the rib.

4. Injection apparatus as claimed in claim 3, wherein a shoulder is provided on the safety needle assembly, which shoulder engages the rib of the sleeve so as to retain the safety needle assembly and injector within the sleeve.

5. Injection apparatus as claimed in claim 1, wherein the co-operable retention means comprises a formation on the outer surface of the safety needle assembly which inter-engages with a corresponding formation on the inner surface of the sleeve, adjacent the closed end thereof.

6. Injection apparatus as claimed in claim 5, wherein the safety needle assembly has a barb-like formation on the outer surface thereof which formation is inter-engageable with a corresponding formation on the inner surface of the sleeve.

7. Injection apparatus as claimed in claim 1, wherein the cap has a closed end and an open end, the open end being inter-engageable with the open end of the sleeve.

8. Injection apparatus as claimed in claim 7, wherein the open end of the cap has an axially-projecting rim which is receivable within the open end of the sleeve.

9. Injection apparatus as claimed in claim 7, wherein there is provided one of a plug-in connection, a screw-threaded connection, a bayonet connection and a snap-fitting connection between the respective open ends of the cap and sleeve.

10. Injection apparatus as claimed in claim 1, wherein the seal means comprises one of a frangible seal and a strippable seal wrapped around the junction between the sleeve and the cap.

11. Injection apparatus as claimed in claim 1, wherein the seal means provides a sterile seal for the injector contained within the sleeve.

12. Injection apparatus as claimed in claim 1, wherein the seal means serves to attach the cap to the sleeve.

13. Injection apparatus as claimed in claim 1, wherein the cap is configured to permit the cap to be refitted to the sleeve following the insertion of a used injector therein.

14. Injection apparatus as claimed in claim 1, wherein the safety needle assembly includes a sleeve which normally is in a projecting position surrounding and protecting the needle, the sleeve being withdrawable from this projecting position to expose the needle and permit the making of an injection.

15. Injection apparatus as claimed in claim 14, wherein the sleeve has a forward position, the sleeve moving to the forward position following withdrawal of the sleeve from the projecting position, and there is provided lock means for automatically locking out the sleeve in the forward position to prevent withdrawal of the sleeve for a second time.

16. Injection apparatus comprising:
   (a) an injector assembly comprising:
      an injector pre-filled with a medicament, said injector comprising a cylindrical body having forward and rearward ends;
      a safety needle assembly provided on said forward end of the cylindrical body, said safety needle assembly comprising a needle in communication with the forward end of the body, an assembly sleeve which normally is in a projecting position surrounding and protecting the needle, the sleeve being withdrawable from this projecting position to expose the needle and permit the making of an injection; and
      a plunger projecting from said rearward end of the cylindrical body and a piston provided on said plunger for expelling medicament out of the safety needle assembly; and
   (b) packaging for said injector assembly comprising:
      a tubular sleeve open at one end and closed at the other end, said sleeve removably receiving said injector therein, said injector initially being located in the tubular sleeve with the plunger nearer the closed end of the tubular sleeve and the safety needle assembly projecting from the open end of the tubular sleeve said sleeve surrounding and enclosing at least the cylindrical body and plunger of said injector;
      a cap having a closed end and an open end, the open end being inter-engageable with the open end of the sleeve and the cap being configured to receive the safety needle assembly when said cap is fitted to the sleeve accommodating the injector;
      seal means for effecting a seal between the sleeve and the cap, said seal means comprising one of a frangible seal and a strippable seal wrapped around the junction between the sleeve and the cap; and
      co-operable retention means for acting between the safety needle assembly sleeve and the inner surface of the tubular sleeve nearer the closed end thereof to retain the safety needle assembly in the sleeve at the closed end thereof;

the arrangement being such that following the breaking of the seal, the injector assembly is removable from the tubular sleeve and the cap is removable from the safety needle assembly so permitting the injector assembly to be used to perform an injection, whereafter the injector assembly is insertable into the tubular sleeve with the safety needle assembly nearer the closed end thereof, the co-operable retention means then serving to retain the safety needle assembly in the tubular sleeve.

* * * * *

UNITED STATES PATENT AND TRADEMARK OFFICE
CERTIFICATE OF CORRECTION

PATENT NO. : 7,815,610 B2  
APPLICATION NO. : 11/675743  
DATED : October 19, 2010  
INVENTOR(S) : Barry Peter Liversidge It is certified that error appears in the above-identified patent and that said Letters Patent is hereby corrected as shown below:

Column 1, line 2, add the following:

CROSS REFERENCE TO RELATED APPLICATION

The present application is a continuation application of International Application PCT/GB2005/003201, filed August 17, 2005, which international application was published on February 23, 2006 as International Publication WO 2006/018626 in the English language. The International Application claims the priority of United Kingdom Patent application 0418389.3, filed August 18, 2004.

Signed and Sealed this
Twenty-eighth Day of February, 2012

David J. Kappos
*Director of the United States Patent and Trademark Office*